(12) United States Patent
Soon et al.

(10) Patent No.: US 8,873,379 B2
(45) Date of Patent: *Oct. 28, 2014

(54) SYSTEM AND METHOD TO ACHIEVE SUB-SECOND ROUTING PERFORMANCE

(75) Inventors: Shih-Chung Tom Soon, Dublin, CA (US); Yongdong Zhao, Pleasanton, CA (US); Teong Yee Tan, Fremont, CA (US); Holly Chen, San Ramon, CA (US); Bei Zhou, Union City, CA (US)

(73) Assignee: AT&T Intellectual Property I, L.P., Atlanta, GA (US)

( * ) Notice: Subject to any disclaimer, the term of this patent is extended or adjusted under 35 U.S.C. 154(b) by 30 days.

This patent is subject to a terminal disclaimer.

(21) Appl. No.: 13/614,732

(22) Filed: Sep. 13, 2012

(65) Prior Publication Data
US 2013/0121138 A1    May 16, 2013

Related U.S. Application Data

(63) Continuation of application No. 11/434,626, filed on May 16, 2006, now Pat. No. 8,295,162.

(51) Int. Cl.
| | |
|---|---|
| *G01R 31/08* | (2006.01) |
| *H04L 12/751* | (2013.01) |
| *H04L 12/701* | (2013.01) |
| *H04L 12/707* | (2013.01) |
| *H04L 12/703* | (2013.01) |
| *H04W 28/04* | (2009.01) |

(52) U.S. Cl.
CPC ............... *H04L 45/28* (2013.01); *H04L 45/02* (2013.01); *H04L 45/00* (2013.01); *H04W 28/04* (2013.01); *H04L 45/22* (2013.01)
USPC ........................................ 370/225

(58) Field of Classification Search
CPC ....................................... H04L 45/28
USPC ............... 370/225, 252–253, 238–238.1, 370/355–356, 392–427
See application file for complete search history.

(56) References Cited

U.S. PATENT DOCUMENTS

| | | |
|---|---|---|
| 4,905,233 A | 2/1990 | Cain et al. |
| 5,016,244 A | 5/1991 | Massey, Jr. et al. |

(Continued)

OTHER PUBLICATIONS

United States Patent and Trademark Office, Final Office Action, issued in connection with U.S. Appl. No. 10/829,539, on Sep. 23, 2010 (32 pages).

(Continued)

*Primary Examiner* — Ricky Ngo
*Assistant Examiner* — Iqbal Zaidi
(74) *Attorney, Agent, or Firm* — Hanley, Flight & Zimmerman, LLC

(57) ABSTRACT

A system and method for routing data, the system having a processor, an interface in communication with the processor and capable of being in communication with a second system for routing data, a memory unit in communication with the processor, the memory unit having a network routing table having a plurality of routes, the plurality of routes having a first route; and a network failure route selection logic including instructions adapted to configure the processor to determine when the first route is inoperative, transmit a first data packet to the second system for routing data when the first route is inoperative and utilize a second route selected from one of the plurality of routes, the second route being different from the first route.

20 Claims, 6 Drawing Sheets

(56) References Cited

U.S. PATENT DOCUMENTS

| | | | |
|---|---|---|---|
| 5,065,392 A | 11/1991 | Sibbitt et al. |
| 5,241,534 A | 8/1993 | Omuro et al. |
| 5,265,092 A | 11/1993 | Soloway et al. |
| 5,375,126 A | 12/1994 | Wallace |
| 5,408,461 A | 4/1995 | Uriu et al. |
| 5,539,817 A | 7/1996 | Wilkes |
| 5,544,170 A | 8/1996 | Kasahara |
| 5,548,639 A | 8/1996 | Ogura et al. |
| 5,559,959 A | 9/1996 | Foglar |
| 5,629,938 A | 5/1997 | Cerciello et al. |
| 5,633,859 A | 5/1997 | Jain et al. |
| 5,650,994 A | 7/1997 | Daley |
| 5,754,527 A | 5/1998 | Fujita |
| 5,764,626 A | 6/1998 | VanDervort |
| 5,774,456 A | 6/1998 | Ellebracht et al. |
| 5,812,528 A | 9/1998 | VanDervort |
| 5,832,197 A | 11/1998 | Houji |
| 5,848,055 A | 12/1998 | Fedyk et al. |
| 5,856,981 A | 1/1999 | Voelker |
| 5,894,475 A | 4/1999 | Bruno et al. |
| 5,926,456 A | 7/1999 | Takano et al. |
| 5,936,939 A | 8/1999 | Des Jardins et al. |
| 6,028,863 A | 2/2000 | Sasagawa et al. |
| 6,038,219 A | 3/2000 | Mawhinney et al. |
| 6,091,951 A | 7/2000 | Sturmiolo et al. |
| 6,104,998 A | 8/2000 | Galand et al. |
| 6,108,300 A | 8/2000 | Coile et al. |
| 6,108,307 A | 8/2000 | McConnell et al. |
| 6,118,763 A | 9/2000 | Trumbull |
| 6,147,998 A | 11/2000 | Kelley et al. |
| 6,167,025 A | 12/2000 | Hsing et al. |
| 6,181,675 B1 | 1/2001 | Miyamoto |
| 6,181,679 B1 | 1/2001 | Ashton et al. |
| 6,185,695 B1 | 2/2001 | Murphy et al. |
| 6,195,416 B1 | 2/2001 | DeCaluwe et al. |
| 6,259,696 B1 | 7/2001 | Yazaki et al. |
| 6,269,401 B1 | 7/2001 | Fletcher et al. |
| 6,311,288 B1 | 10/2001 | Heeren et al. |
| 6,360,260 B1 | 3/2002 | Compliment et al. |
| 6,366,581 B1 | 4/2002 | Jepsen |
| 6,377,548 B1 | 4/2002 | Chuah |
| 6,421,722 B1 | 7/2002 | Bauer et al. |
| 6,424,629 B1 | 7/2002 | Rubino et al. |
| 6,449,259 B1 | 9/2002 | Allain et al. |
| 6,456,306 B1 | 9/2002 | Chin et al. |
| 6,473,398 B1 | 10/2002 | Wall et al. |
| 6,535,990 B1 | 3/2003 | Iterum et al. |
| 6,538,987 B1 | 3/2003 | Cedrone et al. |
| 6,549,533 B1 | 4/2003 | Campbell |
| 6,553,015 B1 | 4/2003 | Sato |
| 6,556,659 B1 | 4/2003 | Bowman-Amuah |
| 6,570,846 B1 | 5/2003 | Ryoo |
| 6,581,166 B1 | 6/2003 | Hirst et al. |
| 6,590,899 B1 | 7/2003 | Thomas et al. |
| 6,594,246 B1 | 7/2003 | Jorgensen |
| 6,594,268 B1 | 7/2003 | Aukia et al. |
| 6,597,689 B1 | 7/2003 | Chiu et al. |
| 6,608,831 B1 | 8/2003 | Beckstrom et al. |
| 6,625,114 B1 | 9/2003 | Hassell |
| 6,643,254 B1 | 11/2003 | Kajitani et al. |
| 6,687,228 B1 | 2/2004 | Fichou et al. |
| 6,697,329 B1 | 2/2004 | McAllister et al. |
| 6,711,125 B1 | 3/2004 | Walrand et al. |
| 6,716,165 B1 | 4/2004 | Flanders et al. |
| 6,738,459 B1 | 5/2004 | Johnstone et al. |
| 6,763,476 B1 | 7/2004 | Dangi et al. |
| 6,766,113 B1 | 7/2004 | Al-Salameh et al. |
| 6,778,525 B1 | 8/2004 | Baum et al. |
| 6,781,952 B2 | 8/2004 | Shirakawa |
| 6,795,393 B1 | 9/2004 | Mazzurco et al. |
| 6,795,394 B1 | 9/2004 | Swinkels et al. |
| 6,810,043 B1 | 10/2004 | Naven et al. |
| 6,823,477 B1 | 11/2004 | Cheng et al. |
| 6,826,184 B1 | 11/2004 | Bryenton et al. |
| 6,829,223 B1 | 12/2004 | Richardson et al. |
| 6,842,513 B1 | 1/2005 | Androski et al. |
| 6,850,483 B1 | 2/2005 | Semaan |
| 6,862,351 B2 | 3/2005 | Taylor |
| 6,865,170 B1 | 3/2005 | Zendle |
| 6,882,652 B1 | 4/2005 | Scholtens et al. |
| 6,885,678 B2 | 4/2005 | Curry et al. |
| 6,925,578 B2 | 8/2005 | Lam et al. |
| 6,952,395 B1 | 10/2005 | Manoharan et al. |
| 6,973,034 B1 | 12/2005 | Natarajan et al. |
| 6,973,037 B1 | 12/2005 | Kahveci |
| 6,978,394 B1 | 12/2005 | Charny et al. |
| 6,981,039 B2 | 12/2005 | Cerami et al. |
| 6,983,401 B2 | 1/2006 | Taylor |
| 6,990,616 B1 | 1/2006 | Botton-Dascal et al. |
| 7,006,443 B2 | 2/2006 | Storr |
| 7,012,898 B1 | 3/2006 | Farris et al. |
| 7,027,053 B2 | 4/2006 | Berndt et al. |
| 7,035,202 B2 | 4/2006 | Callon |
| 7,043,250 B1 | 5/2006 | DeMartino |
| 7,072,331 B2 | 7/2006 | Liu et al. |
| 7,093,155 B2 | 8/2006 | Aoki |
| 7,120,148 B1 | 10/2006 | Batz et al. |
| 7,120,819 B1 | 10/2006 | Gurer et al. |
| 7,146,000 B2 | 12/2006 | Hollman et al. |
| 7,165,192 B1 | 1/2007 | Cadieux et al. |
| 7,184,439 B1 | 2/2007 | Aubuchon et al. |
| 7,200,148 B1 | 4/2007 | Taylor et al. |
| 7,209,452 B2 | 4/2007 | Taylor et al. |
| 7,240,364 B1 | 7/2007 | Branscomb et al. |
| 7,275,192 B2 | 9/2007 | Taylor et al. |
| 7,287,083 B1 | 10/2007 | Nay et al. |
| 7,350,099 B2 | 3/2008 | Taylor et al. |
| 7,391,734 B2 | 6/2008 | Taylor et al. |
| 7,457,233 B1 | 11/2008 | Gan et al. |
| 7,460,468 B2 | 12/2008 | Taylor et al. |
| 7,466,646 B2 | 12/2008 | Taylor et al. |
| 7,469,282 B2 | 12/2008 | Taylor et al. |
| 7,483,370 B1 | 1/2009 | Dayal et al. |
| 7,609,623 B2 | 10/2009 | Taylor et al. |
| 7,630,302 B2 | 12/2009 | Taylor et al. |
| 7,639,606 B2 | 12/2009 | Taylor et al. |
| 7,639,623 B2 | 12/2009 | Taylor et al. |
| 7,646,707 B2 | 1/2010 | Taylor et al. |
| 7,768,904 B2 | 8/2010 | Taylor et al. |
| 7,890,618 B2 | 2/2011 | Taylor et al. |
| 8,031,588 B2 | 10/2011 | Taylor et al. |
| 8,031,620 B2 | 10/2011 | Taylor et al. |
| 8,199,638 B2 | 6/2012 | Taylor et al. |
| 8,200,802 B2 | 6/2012 | Taylor et al. |
| 8,203,933 B2 | 6/2012 | Taylor et al. |
| 8,223,632 B2 | 7/2012 | Taylor et al. |
| 8,243,592 B2 | 8/2012 | Taylor et al. |
| 8,339,938 B2 | 12/2012 | Taylor et al. |
| 8,339,988 B2 | 12/2012 | Taylor et al. |
| 8,345,537 B2 | 1/2013 | Taylor et al. |
| 8,345,543 B2 | 1/2013 | Taylor et al. |
| 2001/0000700 A1 | 5/2001 | Eslambolchi et al. |
| 2001/0010681 A1 | 8/2001 | McAllister et al. |
| 2002/0001307 A1 | 1/2002 | Nguyen et al. |
| 2002/0072358 A1 | 6/2002 | Schneider et al. |
| 2002/0089985 A1 | 7/2002 | Wahl et al. |
| 2002/0112072 A1 | 8/2002 | Jain |
| 2002/0131362 A1* | 9/2002 | Callon ............... 370/216 |
| 2002/0172148 A1 | 11/2002 | Kim et al. |
| 2002/0181402 A1 | 12/2002 | Lemoff et al. |
| 2002/0186653 A1* | 12/2002 | Jensen ............... 370/219 |
| 2003/0043753 A1 | 3/2003 | Nelson et al. |
| 2003/0051049 A1 | 3/2003 | Noy et al. |
| 2003/0051195 A1 | 3/2003 | Bosa et al. |
| 2003/0086413 A1 | 5/2003 | Tartarelli et al. |
| 2003/0091024 A1 | 5/2003 | Stumer |
| 2003/0092390 A1 | 5/2003 | Haumont |
| 2003/0117951 A1 | 6/2003 | Wiebe et al. |
| 2003/0128692 A1 | 7/2003 | Mitsumori et al. |
| 2003/0152028 A1 | 8/2003 | Raisanen et al. |
| 2003/0185151 A1 | 10/2003 | Kurosawa et al. |
| 2004/0090918 A1 | 5/2004 | McLendon |
| 2004/0090973 A1 | 5/2004 | Christie et al. |
| 2004/0125776 A1 | 7/2004 | Haugli et al. |

(56) References Cited

U.S. PATENT DOCUMENTS

| | | | |
|---|---|---|---|
| 2004/0141464 A1 | 7/2004 | Taylor et al. |
| 2004/0143653 A1 | 7/2004 | Taylor et al. |
| 2004/0172574 A1 | 9/2004 | Wing et al. |
| 2004/0202112 A1 | 10/2004 | McAllister et al. |
| 2005/0002339 A1 | 1/2005 | Patil et al. |
| 2005/0013242 A1 | 1/2005 | Chen et al. |
| 2005/0135237 A1 | 6/2005 | Taylor et al. |
| 2005/0135238 A1 | 6/2005 | Taylor et al. |
| 2005/0135254 A1 | 6/2005 | Taylor et al. |
| 2005/0135263 A1 | 6/2005 | Taylor et al. |
| 2005/0138203 A1 | 6/2005 | Taylor et al. |
| 2005/0138476 A1 | 6/2005 | Taylor et al. |
| 2005/0152028 A1 | 7/2005 | Mitzkus |
| 2005/0172160 A1 | 8/2005 | Taylor et al. |
| 2005/0172174 A1 | 8/2005 | Taylor et al. |
| 2005/0237925 A1 | 10/2005 | Taylor et al. |
| 2005/0238006 A1 | 10/2005 | Taylor et al. |
| 2005/0238007 A1 | 10/2005 | Taylor et al. |
| 2005/0238024 A1 | 10/2005 | Taylor et al. |
| 2005/0240840 A1 | 10/2005 | Taylor et al. |
| 2005/0276216 A1 | 12/2005 | Vasseur et al. |
| 2006/0013210 A1 | 1/2006 | Bordogna et al. |
| 2006/0146700 A1 | 7/2006 | Taylor et al. |
| 2006/0153066 A1 | 7/2006 | Saleh et al. |
| 2007/0050492 A1 | 3/2007 | Jorgensen |
| 2007/0168200 A1 | 7/2007 | Shimizu |
| 2007/0268832 A1 | 11/2007 | Soon et al. |
| 2009/0041012 A1 | 2/2009 | Taylor et al. |
| 2009/0086626 A1 | 4/2009 | Taylor et al. |
| 2009/0103544 A1 | 4/2009 | Taylor et al. |
| 2009/0323534 A1 | 12/2009 | Taylor et al. |
| 2010/0020677 A1 | 1/2010 | Taylor et al. |
| 2010/0046366 A1 | 2/2010 | Taylor et al. |
| 2010/0046380 A1 | 2/2010 | Taylor et al. |
| 2010/0054122 A1 | 3/2010 | Taylor et al. |
| 2011/0083045 A1 | 4/2011 | Taylor et al. |

OTHER PUBLICATIONS

United States Patent and Trademark Office, Non-Final Office Action, issued in connection with U.S. Appl. No. 12/254,233, on Apr. 15, 2010 (24 pages).

United States Patent and Trademark Office, Final Office Action, issued in connection with U.S. Appl. No. 12/254,233, on Sep. 29, 2010 (26 pages).

United States Patent and Trademark Office, Non-Final Office Action, issued in connection with U.S. Appl. No. 121334,248, on Apr. 13, 2010 (23 pages).

United States Patent and Trademark Office, Final Office Action, issued in connection with U.S. Appl. No. 12/334,248, on Sep. 29, 2010 (25 pages).

United States Patent and Trademark Office, Non-Final Office Action, issued in connection with U.S. Appl. No. 12/339,426, on Mar. 8, 2010 (6 pages).

United States Patent and Trademark Office, Notice of Allowance, issued in connection with U.S. Appl. No. 12/339,426, on Nov. 8, 2010 (9 pages).

United States Patent and Trademark Office, Non-Final Office Action, issued in connection with U.S. Appl. No. 12/551,477, on Nov. 16, 2010 (15 pages).

United States Patent and Trademark Office, Non-Final Office Action, issued in connection with U.S. Appl. No. 12/570,938, on Oct. 7, 2010 (19 pages).

United States Patent and Trademark Office, Non-Final Office Action, issued in connection with U.S. Appl. No. 12/609,683, on Oct. 25, 2010 (15 pages).

United States Patent and Trademark Office, Non-Final Office Action, issued in connection with U.S. Appl. No. 12/609,640, on Dec. 9, 2010 (11 pages).

United States Patent and Trademark Office, Non-Final Office Action, issued in connection with U.S. Appl. No. 12/609,415, on Dec. 9, 2010 (12 pages).

United States Patent and Trademark Office, Notice of Allowance, issued in connection with U.S. Appl. No. 10/348,592, on Oct. 14, 2008 (4 pages).

United States Patent and Trademark Office, Final Office Action, issued in connection with U.S. Appl. No. 10/348,592, on Mar. 21, 2008 (11 pages).

United States Patent and Trademark Office, Non-Final Office Action, issued in connection with U.S. Appl. No. 10/348,592, on Jun. 14, 2007 (10 pages).

United States Patent and Trademark Office, Notice of Allowance, issued in connection with U.S. Appl. No. 10/829,495, on Apr. 29, 2010 (7 pages).

United States Patent and Trademark Office, Non-Final Office Action, issued in connection with U.S. Appl. No. 10/829,539, on Apr. 27, 2010 (32 pages).

United States Patent and Trademark Office, Non-Final Office Action, issued in connection with U.S. Appl. No. 10/745,170, on Oct. 14, 2009 (23 pages).

United States Patent and Trademark Office, Final Office Action, issued in connection with U.S. Appl. No. 10/745,170, on Apr. 28, 2009 (21 pages).

United States Patent and Trademark Office, Non-Final Office Action, issued in connection with U.S. Appl. No. 10/745,170, on Nov. 14, 2008 (21 pages).

United States Patent and Trademark Office, Non-Final Office Action, issued in connection with U.S. Appl. No. 10/745,170, on Apr. 17, 2008 (14 pages).

United States Patent and Trademark Office, Final Office Action, issued in connection with U.S. Appl. No. 10/829,495, on Mar. 23, 2009 (26 pages).

United States Patent and Trademark Office, Non-Final Office Action, issued in connection with U.S. Appl. No. 10/829,495, on Oct. 29, 2008 (25 pages).

United States Patent and Trademark Office, Final Office Action, issued in connection with U.S. Appl. No. 10/829,495, on Jun. 11, 2008 (22 pages).

United States Patent and Trademark Office, Non-Final Office Action, issued in connection with U.S. Appl. No. 10/829,495, on Sep. 7, 2007 (24 pages).

United States Patent and Trademark Office, Office Action, issued in connection with U.S. Appl. No. 10/829,539 on Mar. 22, 2011 (35 pages).

Meserole, Thomas A. and Prasad, Anil Customer Network Management (CNM) for ATM Public Network Service (M3 Specification), af-nm-0019.000, Rev. 1.04, Oct. 1994 (13 pages).

Chen, Thomas M. and Lin, Steve S., Management and Control Functions in ATM Switching Systems, IEEE Network, Jul./Aug. 1994 (7 pages).

Ryan, Don, The Telco Handbook for New Technicians—An Introduction to Telco Technology and Troubleshooting, Oct. 27, 2000, [retrieved from http://www.darkwing.net/aaronltclco.doc., accessed on Nov. 11, 2006], 67 pages Mangan, Tim, OA&M: How a Frame Relay SLA is Measured and Diagnosed, http://www.mfaforum.org/frame/Whitepaper/whitepapers/OAMwhitepaper.shtml (11 pages).

United States Patent and Trademark Office, Non-Final Office Action, issued in connection with U.S. Appl. No. 10/348,592, on Sep. 8, 2006 (7 pages).

United States Patent and Trademark Office, Notice of Allowance, issued in connection with U.S. Appl. No. 10/744,281, on Oct. 30, 2007 (6 pages).

United States Patent and Trademark Office, Notice of Allowance, issued in connection with U.S. Appl. No. 10/744,281, on Aug. 27, 2007 (6 pages).

United States Patent and Trademark Office, Final Office Action, issued in connection with U.S. Appl. No. 10/744,281, on Apr. 17, 2007 (17 pages).

United States Patent and Trademark Office, Non-Final Office Action, issued in connection with U.S. Appl. No. 10/744,281, on Oct. 2, 2006 (16 pages).

United States Patent and Trademark Office, Notice of Allowance, issued in connection with U.S. Appl. No. 10/744,283, on Sep. 18, 2009 (4 pages).

(56) References Cited

OTHER PUBLICATIONS

United States Patent and Trademark Office, Non-Final Office Action, issued in connection with U.S. Appl. No. 10/744,283, on Apr. 14, 2009 (14 pages).
United States Patent and Trademark Office, Non-Final Office Action, issued in connection with U.S. Appl. No. 10/744,283, on Oct. 30, 2008 (13 pages).
United States Patent and Trademark Office, Final Office Action, issued in connection with U.S. Appl. No. 10/744,283, on Apr. 7, 2008 (II pages).
United States Patent and Trademark Office, Non-Final Office Action, issued in connection with U.S. Appl. No. 10/744,283, on Jul. 20, 2007 (12 pages).
United States Patent and Trademark Office, Office Action, issued in connection with U.S. Appl. No. 10/744,555 on Aug. 6, 2007 (18 pages).
United States Patent and Trademark Office, Office Action, issued in connection with U.S. Appl. No. 10/744,555 on May 12, 2008 (32 pages).
United States Patent and Trademark Office, Office Action, issued in connection with U.S. Appl. No. 10/744,555 on Jan. 14, 2009 (37 pages).
United States Patent and Trademark Office, Office Action, issued in connection with U.S. Appl. No. 10/744,555 on Jul. 17, 2009 (27 pages).
United States Patent and Trademark Office, Office Action, issued in connection with U.S. Appl. No. 10/744,555 on Apr. 14, 2011 (19 pages).
United States Patent and Trademark Office, Office Action, issued in connection with U.S. Appl. No. 10/744,921 on Aug. 8, 2007 (16 pages).
United States Patent and Trademark Office, Office Action, issued in connection with U.S. Appl. No. 10/744,921 on May 1, 2008 (24 pages).
United States Patent and Trademark Office, Office Action, issued in connection with U.S. Appl. No. 10/744,921 on Oct. 31, 2008 (23 pages).
United States Patent and Trademark Office, Office Action, issued in connection with U.S. Appl. No. 10/744,921 on Apr. 6, 2009 (23 pages).
United States Patent and Trademark Office, Office Action, issued in connection with U.S. Appl. No. 10/744,921 on Jul. 9, 2009 (24 pages).
United States Patent and Trademark Office, Office Action, issued in connection with U.S. Appl. No. 10/744,921 on May 11, 2011 (20 pages).
United States Patent and Trademark Office, Final Office Action, issued in connection with U.S. Appl. No. 10/745,047, on Mar. 27, 2009 (19 pages).
United States Patent and Trademark Office, Non-Final Office Action, issued in connection with U.S. Appl. No. 10/745,047, on Jun. 12, 2008 (18 pages).
United States Patent and Trademark Office, Notice of Allowance, issued in connection with U.S. Appl. No. 10/745,047, on Jul. 23, 2009 (7 pages).
United States Patent and Trademark Office, Notice of Allowance, issued in connection with U.S. Appl. No. 10/745,116, on Aug. 14, 2009 (7 pages).
United States Patent and Trademark Office, Notice of Allowance, issued in connection with U.S. Appl. No. 10/745,116, on May 7, 2009 (8 pages).
United States Patent and Trademark Office, Final Office Action, issued in connection with U.S. Appl. No. 10/745,116, on Apr. 28, 2008 (25 pages).
United States Patent and Trademark Office, Notice of Allowance, issued in connection with U.S Appl. No. 10/745,116, on Dec. 3, 2008 (8 pages).
United States Patent and Trademark Office, Non-Final Office Action, issued in connection with U.S. Appl. No. 10/745,116, on Aug. 7, 2007 (20 pages).
United States Patent and Trademark Office, Notice of Allowance, issued in connection with U.S Appl. No. 10/745,117, on May 14, 2009 (8 pages).
United States Patent and Trademark Office, Non-Final Office Action, issued in connection with U.S. Appl. No. 10/745,117, on Nov. 26, 2008 (20 pages).
United States Patent and Trademark Office, Final Office Action, issued in connection with U.S. Appl. No. 10/745,117, on May 12, 2008 (15 pages).
United States Patent and Trademark Office, Non-Final Office Action, issued in connection with U.S. Appl. No. 10/745,117, on Apr. 17, 2008 (15 pages).
United States Patent and Trademark Office, Non-Final Office Action, issued in connection with U.S. Appl. No. 10/745,117, on Aug. 8, 2007 (14 pages).
United States Patent and Trademark Office, Supplemental Notice of Allowance, issued in connection with U.S. Appl. No. 10/745,117, on Jun. 15, 2009 (4 pages).
United States Patent and Trademark Office, Notice of Allowance, issued in connection with U.S. Appl. No. 10/745,117, on Aug. 27, 2009 (7 pages).
United States Patent and Trademark Office, Non-Final Office Action, issued in connection with U.S. Appl. No. 10/745,168, on Dec. 2, 2008 (24 pages).
United States Patent and Trademark Office, Final Office Action, issued in connection with U.S. Appl. No. 10/745,168, on May 2, 2008 (21 pages).
United States Patent and Trademark Office, Final Office Action, issued in connection with U.S. Appl. No. 10/745,168, on Aug. 8, 2007 (17 pages).
United States Patent and Trademark Office, Notice of Allowance, issued in connection with U.S. Appl. No. 10/745,168, on Jun. 12, 2009 (9 pages).
United States Patent and Trademark Office, Notice of Allowance, issued in connection with U.S. Appl. No. 10/745,168, on Aug. 7, 2009 (7 pages).
United States Patent and Trademark Office, Notice of Allowance, issued in connection with U.S. Appl. No. 10/745,170 on Dec. 27, 2011 (7 pages).
United States Patent and Trademark Office, Office Action, issued in connection with U.S. Appl. No. 10/745,170 on Jul. 20, 2007 (14 pages).
United States Patent and Trademark Office, Final Office Action, issued in connection with U.S. Appl. No. 10/744,555, on Oct. 7, 2010 (26 pages).
United States Patent and Trademark Office, Non-Final Office Action, issued in connection with U.S. Appl. No. 10/744,555, on Feb. 1, 2010 (26 pages).
United States Patent and Trademark Office, Final Office Action, issued in connection with U.S. Appl. No. 10/744,921, on Mar. 3, 2010 (23 pages).
United States Patent and Trademark Office, Final Office Action, issued in connection with U.S. Appl. No. 10/745,170, on Oct. 26, 2010 (24 pages).
United States Patent and Trademark Office, Non-Final Office Action, issued in connection with U.S. Appl. No. 10/745,170, on Mar. 30, 2010 (24 pages).
United States Patent and Trademark Office, Notice of Allowance, issued in connection with U.S. Appl. No. 10/829,539, mailed on Aug. 16, 2012 (8 pages).
United States Patent and Trademark Office, Notice of Allowance, issued in connection with U.S. Appl. No. 12/254,233, mailed on Aug. 16, 2012 (9 pages).
United States Patent and Trademark Office, Notice of Allowance, issued in connection with U.S. Appl. No. 12/334,248, mailed on Aug. 22, 2012 (9 pages).
United States Patent and Trademark Office, Notice of Allowance, issued in connection with U.S. Appl. No. 12/609,415, mailed on Aug. 22, 2012 (8 pages).
United States Patent and Trademark Office, Non-Final Office Action, issued in connection with U.S. Appl. No. 10/829,539, on Jan. 30, 2012 (37 pages).

(56) References Cited

OTHER PUBLICATIONS

United States Patent and Trademark Office, Non-Final Office Action, issued in connection with U.S. Appl. No. 12/254,233, on Jan. 30, 2012 (29 pages).
United States Patent and Trademark Office, Non-Final Office Action, issued in connection with U.S. Appl. No. 12/334,248, on Jan. 30, 2012 (29 pages).
United States Patent and Trademark Office, Notice of Allowance, issued in connection with U.S. Appl. No. 12/967,930, on Jan. 30, 2012 (13 pages).
United States Patent and Trademark Office, Notice of Allowance, issued in connection with U.S. Appl. No. 10/744,555, on Feb. 6, 2012 (8 pages).
United States Patent and Trademark Office, Notice of Allowance, issued in connection with U.S. Appl. No. 12/551,477, on Mar. 1, 2012 (8 pages).
United States Patent and Trademark Office, Final Office Action, issued in connection with U.S. Appl. No. 12/609,415, on Mar. 7, 2012 (12 pages).
United States Patent and Trademark Office, Notice of Allowance, issued in connection with U.S. Appl. No. 10/745,170, on Mar. 30, 2012 (7 pages).
United States Patent and Trademark Office, Notice of Allowance, issued in connection with U.S. Appl. No. 10/744,921, on Apr. 23, 2012 (19 pages).
United States Patent and Trademark Office, Advisory Action, issued in connection with U.S. Appl. No. 10/829,495 on Jun. 4, 2009 (3 pages).
United States Patent and Trademark Office, Office Action, issued in connection with U.S. Appl. No. 10/829,495 on Oct. 1, 2009 (24 pages).
United States Patent and Trademark Office, Notice of Allowance, issued in connection with U.S. Appl. No. 10/829,509, on Jul. 10, 2007 (7 pages).
United States Patent and Trademark Office, Notice of Allowance, issued in connection with U.S. Appl. No. 10/829,509, on Feb. 1, 2007 (8 pages).
United States Patent and Trademark Office, Final Office Action, issued in connection with U.S. Appl. No. 10/829,509, on Nov. 13, 2006 (12 pages).
United States Patent and Trademark Office, Non-Final Office Action, issued in connection with U.S. Appl. No. 10/829,509, on May 15, 2006 (11 pages).
United States Patent and Trademark Office, Office Action, issued in connection with U.S. Appl. No. 10/829,539 on Oct. 17, 2007 (19 pages).
United States Patent and Trademark Office, Office Action, issued in connection with U.S. Appl. No. 10/829,539 on Aug. 20, 2008 (29 pages).
United States Patent and Trademark Office, Office Action, issued in connection with U.S. Appl. No. 10/829,539 on Nov. 25, 2008 (23 pages).
United States Patent and Trademark Office, Office Action, issued in connection with U.S. Appl. No. 10/829,539 on Mar. 13, 2009 (30 pages).
United States Patent and Trademark Office, Advisory Action, issued in connection with U.S. Appl. No. 10/829,539 on Jun. 12, 2009 (3 pages).
United States Patent and Trademark Office, Office Action, issued in connection with U.S. Appl. No. 10/829,539 on Aug. 25, 2009 (42 pages).
United States Patent and Trademark Office, Office Action, issued in connection with U.S. Appl. No. 10/829,539 on Sep. 29, 2011 (37 pages).
United States Patent and Trademark Office, Notice of Allowance, issued in connection with U.S. Appl. No. 10/829,584, on Sep. 22, 2008 (7 pages).
United States Patent and Trademark Office, Final Office Action issued in connection with U.S. Appl. No. 10/829,584, on Jun. 25, 2008 (20 pages).
United States Patent and Trademark Office, Non-Final Office Action, issued in connection with U.S. Appl. No. 10/829,584, on Sep. 19, 2007 (15 pages).
United States Patent and Trademark Office, Supplemental Notice of Allowance, issued in connection with U.S. Appl. No. 10/829,795, on Nov. 13, 2008 (2 pages).
United States Patent and Trademark Office, Notice of Allowance, issued in connection with U.S. Appl. No. 10/829,795, on Sep. 9, 2008 (7 pages).
United States Patent and Trademark Office, Final Office Action, issued in connection with U.S. Appl. No. 10/829,795, on Apr. 30, 2008 (20 pages).
United States Patent and Trademark Office, Non-Final Office Action, issued in connection with U.S. Appl. No. 10/829,795, on Sep. 10, 2007 (21 pages).
United States Patent and Trademark Office, Office Action, issued in connection with U.S. Appl. No. 12/254,233 on Mar. 25, 2011 (28 pages).
United States Patent and Trademark Office, Office Action, issued in connection with U.S. Appl. No. 12/254,233 on Oct. 3, 2011 (29 pages).
United States Patent and Trademark Office, Office Action, issued in connection with U.S. Appl. No. 12/334,248 on Mar. 25, 2011 (28 pages).
United States Patent and Trademark Office, Office Action, issued in connection with U.S. Appl. No. 12/334,248 on Oct. 3, 2011 (29 pages).
United States Patent and Trademark Office, Office Action, issued in connection with U.S. Appl. No. 12/551,477 on Jul. 11, 2011 (13 pages).
United States Patent and Trademark Office, Notice of Allowance, issued in connection with U.S. Appl. No. 12/570,938 on Jun. 20, 2011 (7 pages).
United States Patent and Trademark Office, Supplemental Notice of Allowance, issued in connection with U.S. Appl. No. 12/570,938 on Aug. 23, 2011 (5 pages).
United States Patent and Trademark Office, Office Action, issued in connection with U.S. Appl. No. 12/609,415 on Jun. 23, 2011 (12 pages).
United States Patent and Trademark Office, Notice of Abandonment, issued in connection with U.S. Appl. No. 12/609,640 on Jun. 20, 2011 (2 pages).
United States Patent and Trademark Office, Notice of Allowance, issued in connection with U.S. Appl. No. 12/609,683 on Jul. 12, 2011 (7 pages).
United States Patent and Trademark Office, Office Action, issued in connection with U.S. Appl. No. 12/967,930 on Apr. 29, 2011 (6 pages).
United States Patent and Trademark Office, Non-Final Office Action, issued in connection with U.S. Appl. No. 10/348,077, on Jan. 4, 2007 (16 pages).
United States Patent and Trademark Office, Final Office Action, issued in connection with U.S. Appl. No. 10/348,077, on Aug. 10, 2007 (26 pages).
United States Patent and Trademark Office, Notice of Allowance, issued in connection with U.S. Appl. No. 10/348,077, on Apr. 29, 2008 (10 pages).

\* cited by examiner

SYSTEM AND METHOD TO ACHIEVE SUB-SECOND ROUTING PERFORMANCE

RELATED APPLICATION(S)

This patent arises from a continuation of U.S. Application Ser. No. 11/434,626, entitled "SYSTEM AND METHOD TO ACHIEVE SUB-SECOND ROUTING PERFORMANCE" and filed on May 16, 2006, which is hereby incorporated by reference in its entirety.

TECHNICAL FIELD

The present disclosure generally relates to methods and systems for routing data on a network.

BACKGROUND

Dynamic routing protocols are widely used in broadband networks to route data packets. One of the functions of these dynamic routing protocols, besides establishing the initial routing, is to reroute data packets around network failures. In the past, rerouting data involves a procedure that may take several minutes from the time the network failure occurs to the time the new routes are installed in the routing tables of the nodes, routers or switches that encompass the network.

Time sensitive network traffic, such as network traffic including voice over internet protocol ("VoIP") telephone calls and real time audio and video transmissions, are sensitive to network failures. For example, if a VoIP telephone call is interrupted by a network failure, the VoIP telephone call will likely be dropped because the rerouting around the network failure may take several minutes. This has the unfortunate drawback of requiring VoIP telephone users to redial to reestablish their telephone calls affected by the network failure. In like manner, real time streaming of audio and video may be interrupted for several minutes while the network reroutes around the network failure. The time taken to reroute around the network failure may significantly reduce the user's ability to effectively utilize network services. Therefore, there exists a need for a system that can more efficiently reroute around network failures.

DETAILED DESCRIPTION

In order to address the drawbacks of current data routing systems, a suitable system for routing data may include a processor, an interface in communication with the processor and capable of being in communication with a second system for routing data, a memory unit in communication with the processor, the memory unit having a network routing table having a plurality of routes, the plurality of routes having a first route, and a network failure route selection logic including instructions adapted to configure the processor to determine when the first route is inoperative, transmit a first data packet to the second system for routing data when the first route is inoperative and utilize a second route selected from one of the plurality of routes, the second route being different from the first route. These and other aspects and advantages are described in greater detail below.

Figure 1:
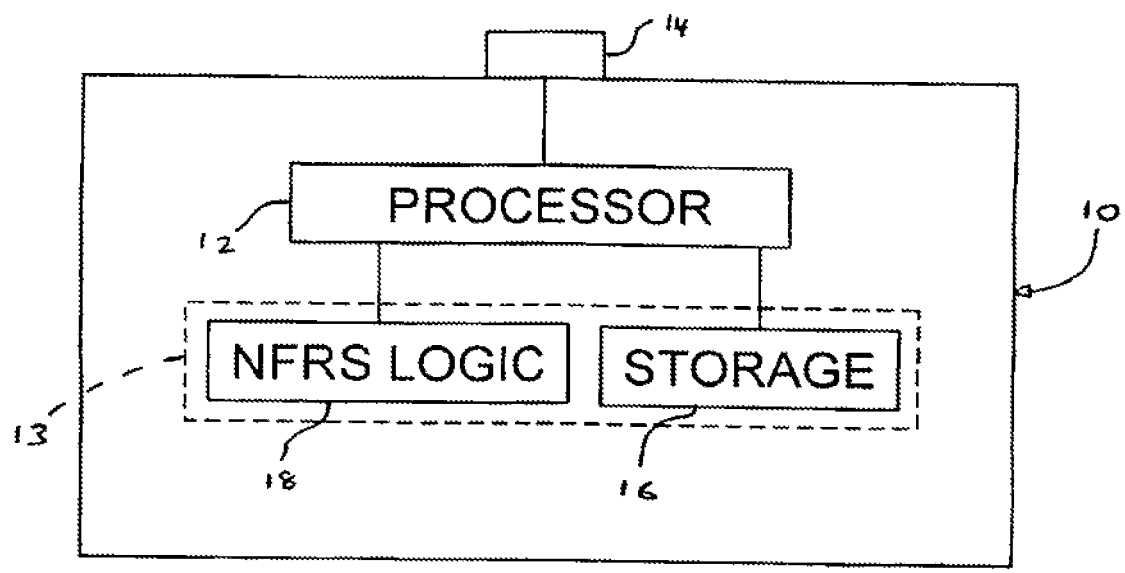
FIG. 1 is a block diagram of an embodiment of a system for routing data.

Referring to FIG. 1, a system 10 for routing data is shown. The system 10 may be a router commonly used to route data on a computer network. The system 10 includes a processor 12 in communication with an interface 14, a storage device 16 and network failure route selection ("NFRS") logic 18. The interface 14 is an interface capable of being connected to a computer network such as an Ethernet interface. This configuration is typical of a router for a computer network.

The storage device 16 may be a solid state storage device as found in a typical router. However, the storage device 16 may further be a magnetic storage device or an optical storage device. The storage device 16 may be a discrete device or integrated within the processor 12. Additionally, the NFRS logic 18 and the storage device 16 may be separate modules integrated into a common memory unit 13. The NFRS logic 18 may include instructions adapted to configure the processor 12 to implement a data routing method which will be later described in this description.

The memory unit 16 may contain a network routing table. Routing is a concept of the Internet and many other networks. Routing provides the means of discovering paths along which information, such as data packets can be sent. The network routing table contains information for numerous routes that is used to determine which route to utilize so that a data packet may be transmitted to the data packet's destination.

Figure 2:
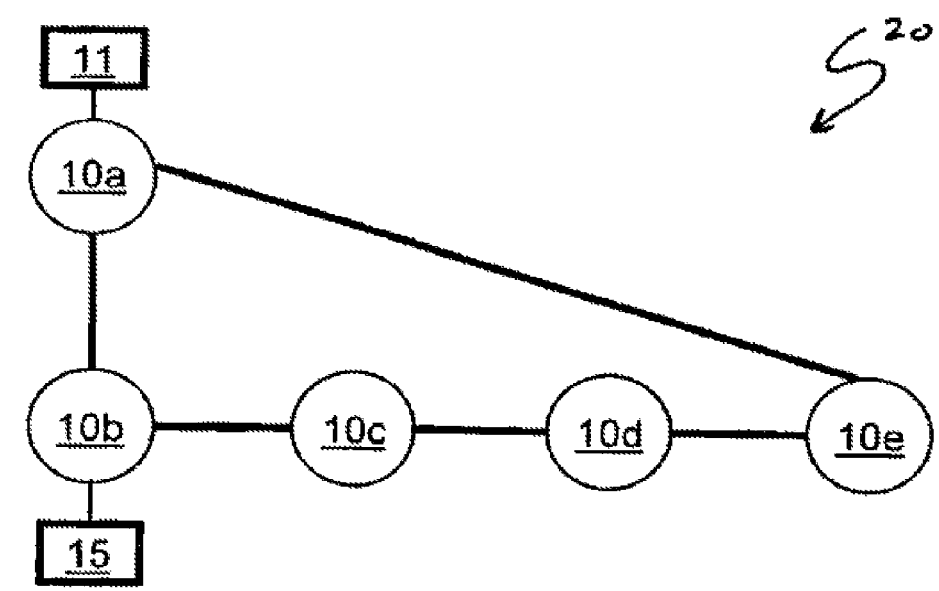
FIG. 2 is a block diagram of a network within which the system of FIG. 1 may operate.

Referring to FIGS. 1 and 2, the system 10 may be implemented in a computer network 20. The computer network 20 may be a local area network or may be a wide area network. For exemplary purposes, the network 20 may include systems 10a, 10b, 10c, 10d and 10e. Systems 10a, 10b, 10c, 10d and 10e may be similar to the system 10 described in FIG. 1. Systems 10a, 10b, 10c, 10d and 10e are connected to each other via their respective interface 14 (as best shown in FIG. 1) using a network cable or a wireless communication system such as IEEE 802.11g. In this example, system 10a is connected to system 10b and system 10e. System 10c is connected system 10b and system 10d. System 10d is connected to system 10c system 10e.

Figure 3:
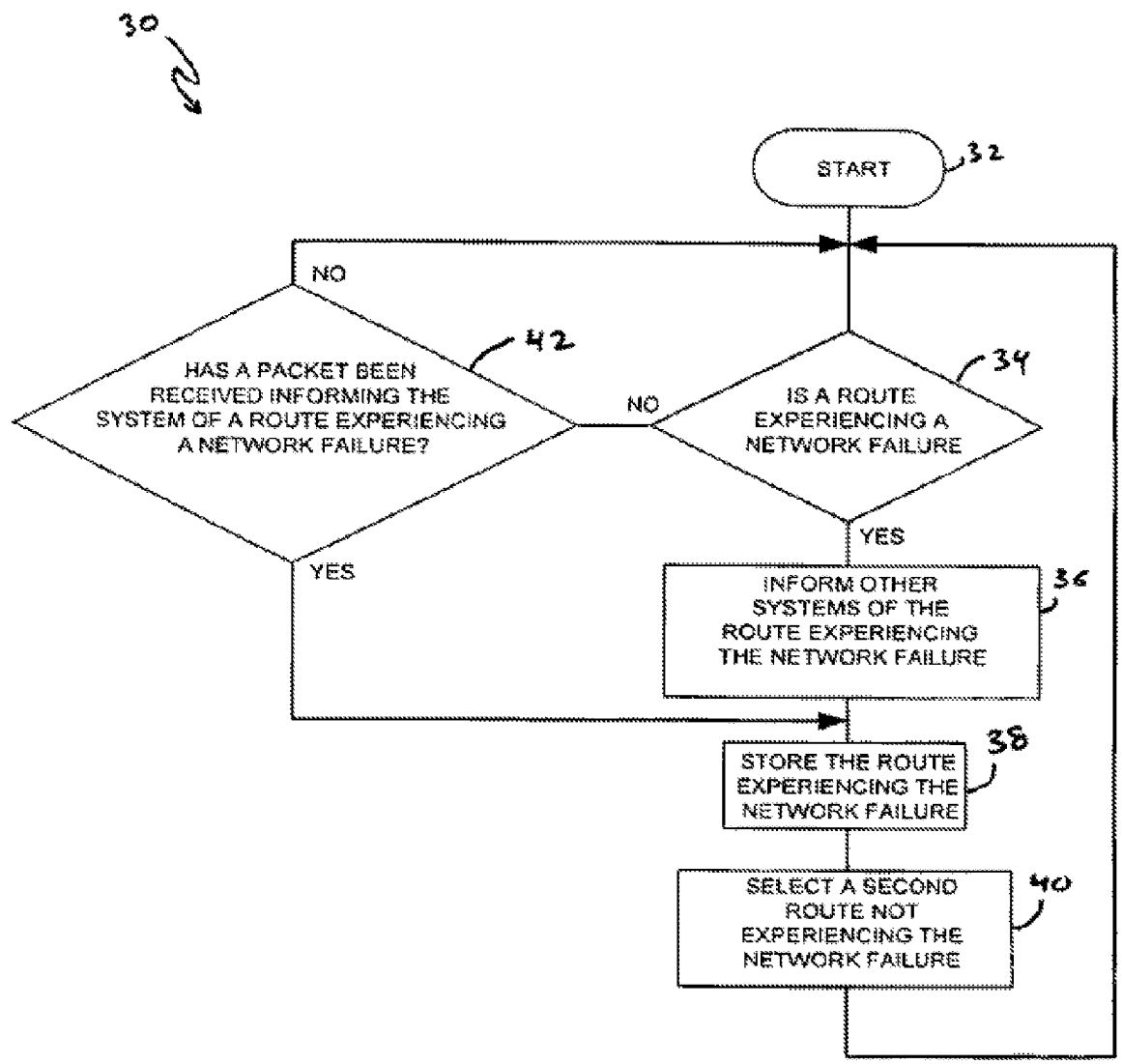
FIG. 3 is a block diagram of a flow chart illustrating one method the system of FIG. 1.

Referring to FIGS. 1 and 3, a fast reroute protocol ("FRRP") method 30 for routing data is shown. The method 30 may be contained within the NFRS logic 18 and may be executed by the processor 12. Block 32 indicates the starting point of the method. As shown in block 34, the method 30 first determines if a one of the routes in the routing table and utilized by the system 10 has a network failure. This network failure may be a link layer failure or a protocol layer failure. These failures may be detected by losing a signal for a period of time or a link layer detection scheme.

Moving to block 36, once a network failure has been detected, a data packet is sent to the other systems. This data packet contains the identity route wherein the network failure has occurred. In addition, the data packet may include additional information such as the type of network failure. The type of network failure may be a link failure or a nodal failure.

Next, as shown in block 38, once the other systems have been informed of the network failure, the route experiencing the network failure information is stored. This may be accomplished by storing the network failure information in the storage device 16. Afterwards, a new route is selected from the routing table and utilized. The selection process will consider any of the routes containing within the routing table with the exception of any routes experiencing a network failure. The selection process is based on route data structures. More specifically, the method 30 may allow certain routes to participate in the route calculation and disable some other routes from being used in the route calculation process. In essence, a function of this recalculation is to allow/disallow certain routes to be used by recalculation process. By so doing, the system 10 will avoid using the route experiencing the network failure when transmitting data. Thereafter, this process repeats as new routes experiencing a network failure are discovered.

In block 42, if a network failure is not detected as shown in block 34, a determination is made if another system has sent a multicasted data packet indicating that a route is experiencing a network failure. If this occurs, the network failure information is stored and a new routing is selected as shown in blocks 40, 42. Afterwards, process repeats as new routes experiencing a network failure are discovered. It should be understood that more than one route may be stored. By so doing, routes experiencing failures may be excluded from the selection process.

Each multicasted data packet may contain (1) identity of the system detecting the network failure, (2) an indication of the type of network failures detected and (3) a sequence number which may be used to identify the instance of the fast reroute request from each system.

Each system may keep a table to track the multicasted packet received from its peers. The table stores the system detecting the failure. When the multicasted packet is received, the system shall perform the following tasks: (1) examine the multicasted packet process ID to ensure this multicasted packet is from a peer, (2) compare the packet sequence number from the received packet to the sequence number stored in the sequence tracking table, (3) if the sequence number is not newer than the stored sequence number, the received multicasted packet shall be discarded without being further forwarded, (4) if the sequence number of the received multicasted packet is newer than the stored sequence number, then the sequence tracking table is updated with the new sequence number, (5) flood the multicasted packet to all the other systems except the one the packet was received, and (6) update the NFRS logic and utilize a route indicated by the NFRS logic.

Referring to FIG. 2, an example of how method 30 operates will be described. Assume a first host 15 connected to system 10b is attempting to transmit data to and/or from a second host 11, which is connected to system 10a. The first host 15 via system 10b will transmit information to the second host 11 via the system 10a. However, in the occurrence that the communication link between system 10a and system 10b is broken, the system 10b will send a data packet notifying all the other systems 10a, 10c, 10d and 10e of the broken link. Afterwards, the systems 10a, 10b, 10c, 10d and 10e will store this broken link information and select a route from the routing table. Thereafter, the system 10b will transmit data to the second host 11 via systems 10c, 10d, 10e, 10a.

Figure 4:
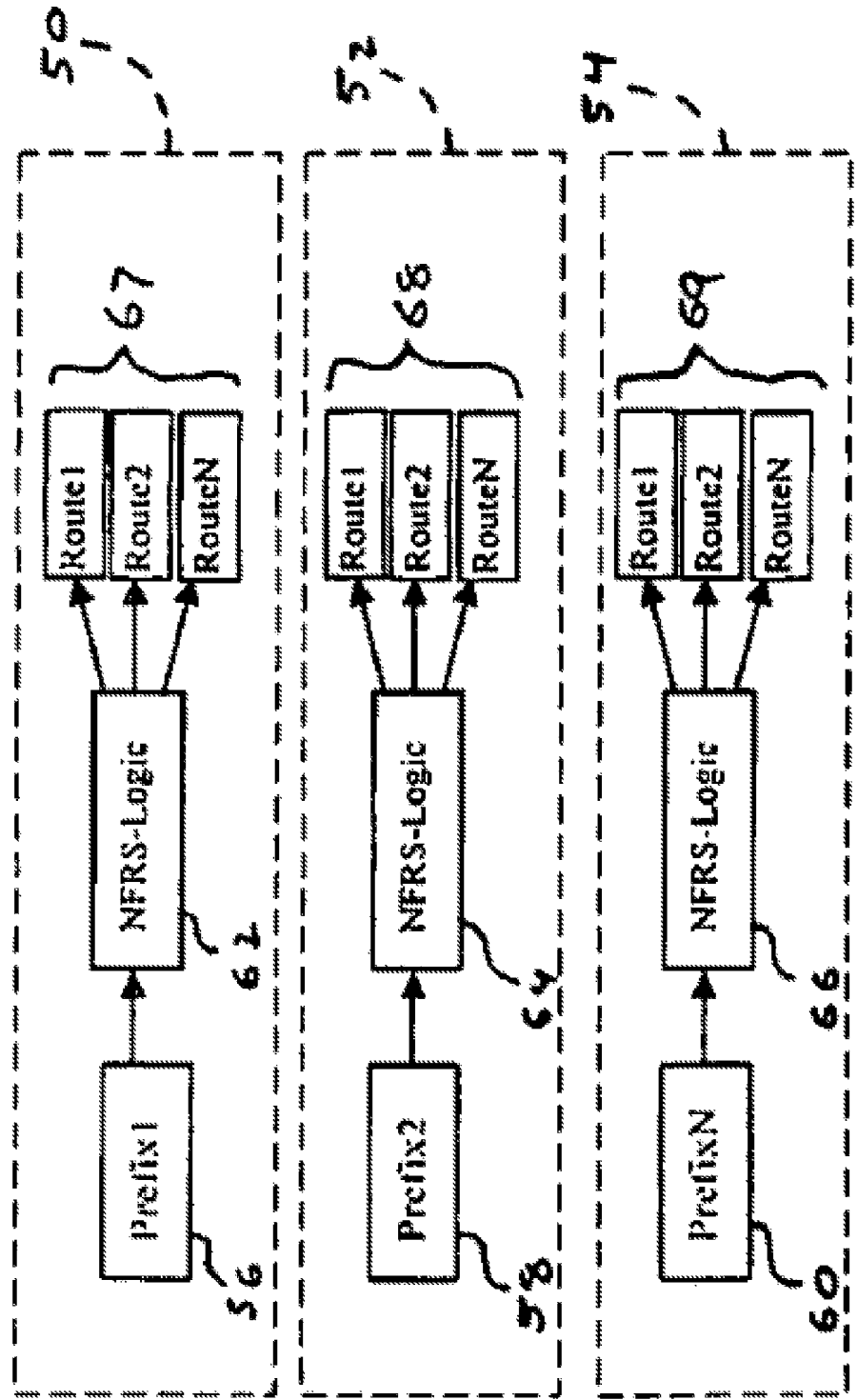
FIG. 4 is a block diagram of a routing table.

Referring to FIG. 4, a first, second and third routing tables 50, 52, 54 utilizing the method 30 of FIG. 3 are shown. The three routing tables 50, 52, 54 are shown for exemplary purposes. Any number of routing tables may be utilized. The routing tables 50, 52, 54 each include prefixes 56, 58, 60, NFRS Logics 62, 64, 66. To route a data packet, the NFRS Logics 56, 58, 60 select one of routes 67, 68, 69, respectively during a failure condition.

Figure 5:
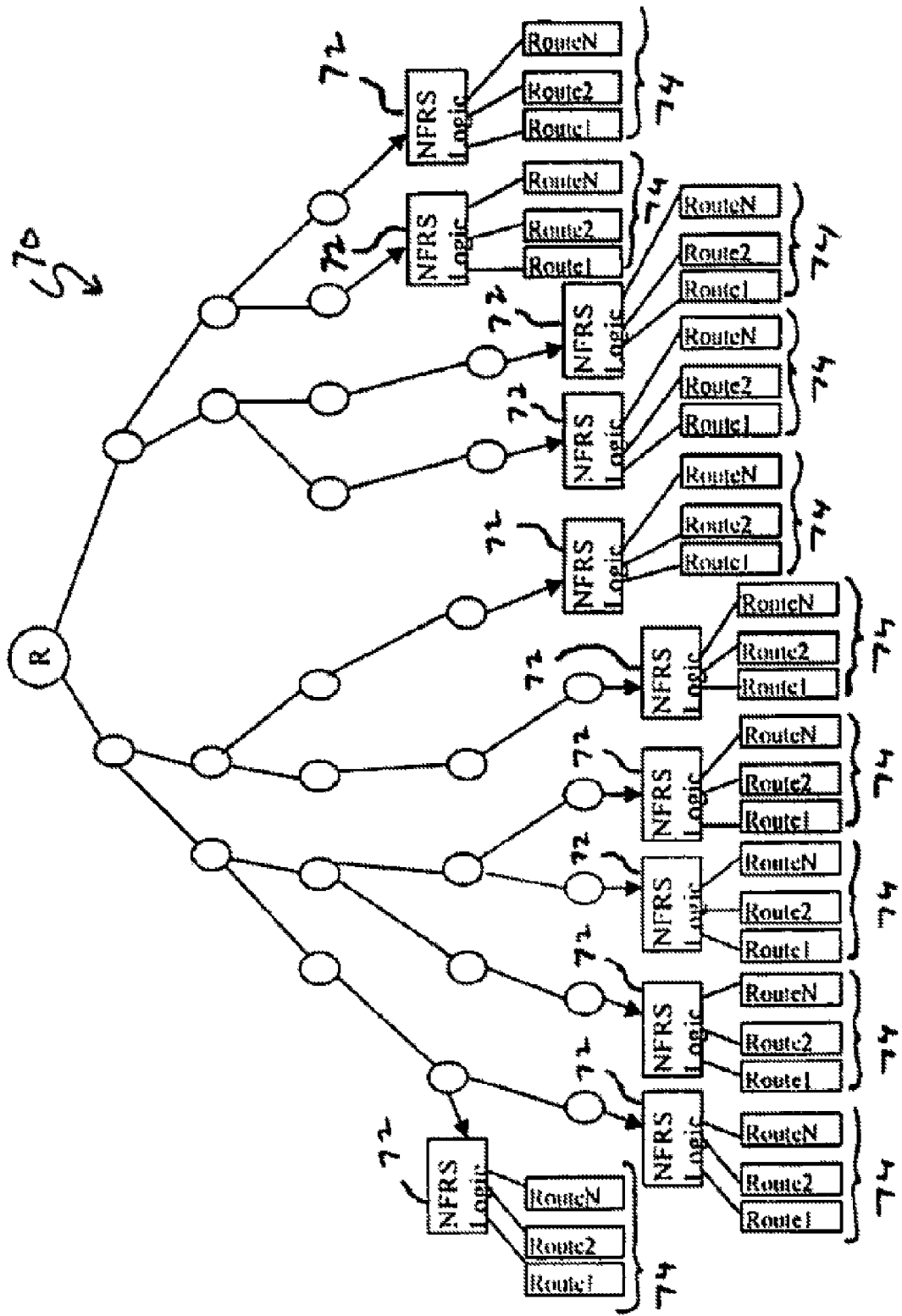
FIG. 5 is a TRIE structure incorporating the present invention.
Figure 6:
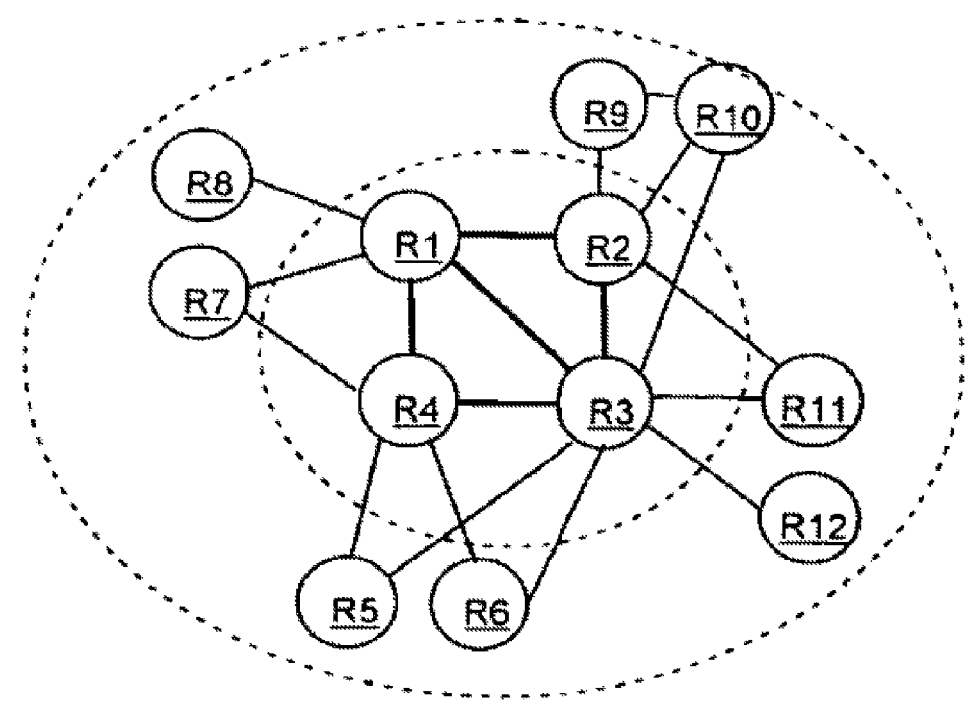
FIG. 6 is a network utilizing a fast rerouting scheme.

Referring to FIG. 5, an NFRS logic 72 embedded in a TRIE structure 70. As stated previously, the NFRS logic 72 will select of the routes 74. The search of the longest prefix match is combined and controlled by the NFRS logic 72. NFRS logic 72 chooses the best route based on the network failure conditions. When network failures are detected and fast rerouting request is issued, all the routers shall save the network failure condition in the NFRS logic. The NFRS logic selection logic is implemented at each router independently and yields a consistent decision for selecting a route that warrants network-wide routing integrity and completeness under the failures. Use hardware/software failure indication to directly trigger the FRRP. This step skips the traditional failure confirmation, link state update, topology database convergence and route recalculation stages to significantly reduce the rerouting latency. Implement the method 30 to promptly invoke rerouting by updating the NFRS logic 72 at each node of the protected domain where the network failures occurred. The FRRP ensures the consistence of all the NFRS logic for all of the routers in a protected domain Referring to FIG. 6, the FRRP method 30 may be used to protect an entire network or may be used to protect selected portions of the network for better scalability. More specifically, the FRRP method 30 may be utilized in nodes R1, R2, R3, R4. The network shown in FIG. 6 can be partitioned into several rerouting domains, each rerouting domain covering a subset of the network. The system can have all its ports utilized in the method or it can have just a subset of its ports utilizing the method. There could also be several overlaps between different routing domains. For instance, a system can have a set of ports in one routing domain and a set of ports in another routing domain. Each node can belong to multiple routing domains. The purpose of partitioning the entire network into separate rerouting domains is to constrain the network complexity to simplify the HFRS logic and speed up the rerouting process. The rerouting domains can be structured to span the entire network or only selected portions of the network. The FRRP protocol will be bounded by the rerouting domains for better scalability.

For example, nodes R1, R8 and R7 are a first routing domain. Nodes R3, R11 and R12 are a second routing domain. Nodes R4, R5 and R6 are a third routing domain. Nodes R2, R9 and R10 are a fourth routing domain. Finally, nodes R1, R2, R3 and R4 make up a fifth routing domain. As stated previously, by partitioning the network into these different routing domains the network complexity will be simplified speeding up the rerouting process.

Figure 7:
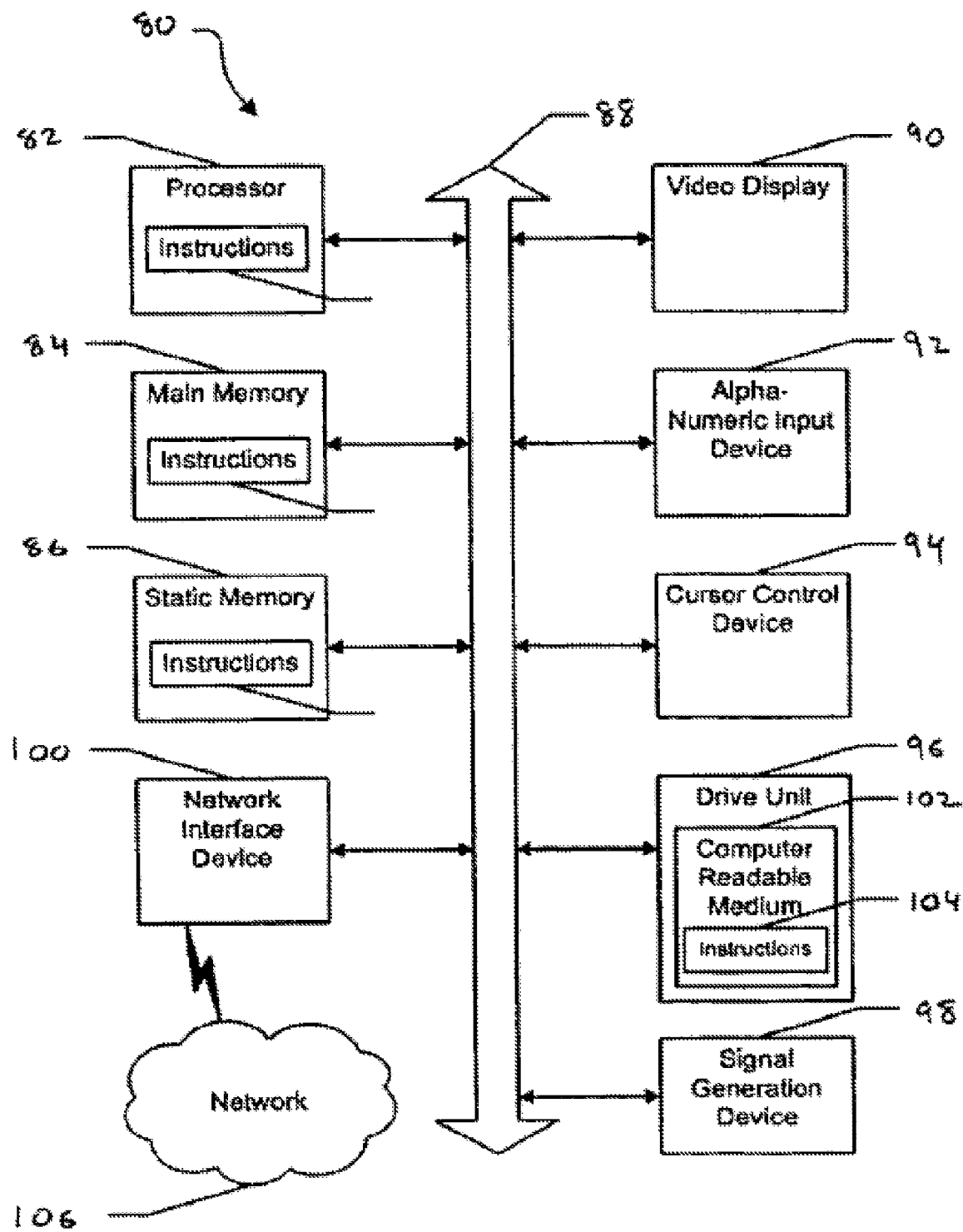
FIG. 7 is a block diagram of a general purpose computer suitable for use in implementing the system and method described herein.

Referring to FIG. 7, an illustrative embodiment of a general computer system is shown and is designated 80. The computer system 80 can include a set of instructions that can be executed to cause the computer system 80 to perform any one or more of the methods or computer based functions disclosed herein. The computer system 80 may operate as a standalone device or may be connected, e.g., using a network, to other computer systems or peripheral devices.

In a networked deployment, the computer system may operate in the capacity of a server or as a client user computer in a server-client user network environment, or as a peer computer system in a peer-to-peer (or distributed) network environment. The computer system 80 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In a particular embodiment, the computer system 80 can be implemented using electronic devices that provide voice, video or data communication. Further, while a single computer system 80 is illustrated, the term "system" shall also be taken to include any collection of systems or sub-systems that individually or jointly execute a set, or multiple sets, of instructions to perform one or more computer functions.

As illustrated in FIG. 7, the computer system 80 may include a processor 82, e.g., a central processing unit (CPU), a graphics processing unit (GPU), or both. Moreover, the computer system 80 can include a main memory 84 and a static memory 86 that can communicate with each other via a bus 88. As shown, the computer system 80 may further include a video display unit 90, such as a liquid crystal display (LCD), an organic light emitting diode (OLED), a flat panel display, a solid state display, or a cathode ray tube (CRT). Additionally, the computer system 80 may include an input device 92, such as a keyboard, and a cursor control device 94, such as a mouse. The computer system 80 can also include a disk drive unit 96, a signal generation device 98, such as a speaker or remote control, and a network interface device 100.

In a particular embodiment, as depicted in FIG. 7, the disk drive unit 96 may include a computer-readable medium 102 in which one or more sets of instructions 104, e.g. software, can be embedded. Further, the instructions 104 may embody one or more of the methods or logic as described herein. In a particular embodiment, the instructions 104 may reside completely, or at least partially, within the main memory 84, the static memory 86, and/or within 84 and the processor 82 also may include computer-readable media.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

The present disclosure contemplates a computer-readable medium that includes instructions 104 or receives and executes instructions 104 responsive to a propagated signal, so that a device connected to a network 106 can communicate voice, video or data over the network 106. Further, the instructions 104 may be transmitted or received over the network 106 via the network interface device 100.

While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A method for a first router, the method comprising:
   determining, using a processor, whether a sequence number included in a first reroute request received from a second router is newer than a stored sequence number associated with the second router, the first reroute request including network failure information identifying a cause of a failure of a first route, the sequence number being incremented for each new reroute request sent from the second router; and
   selecting, using the processor, a second route from a plurality of routes to carry data in place of the first route if the sequence number included in the first reroute request is determined to be newer than the stored sequence number but not if the sequence number included in the first reroute request is determined to be older than the stored sequence number, the plurality of routes being stored in a routing table, the second route being different from the first route.

2. The method as defined in claim 1 wherein the first reroute request comprises information related to a condition of the first route.

3. The method as defined in claim 1 further comprising determining a cause of a failure of a third route by detecting a loss of a signal along the third route.

4. The method as defined in claim 1 further comprising determining a cause of a failure of a third route by using a link layer failure detection scheme.

5. The method as defined in claim 1 further comprising sending a second reroute request to a third system, the second reroute request including information related to a condition of the first route.

6. The method as defined in claim 1 further comprising selecting the second route based on the cause of the failure.

7. The method as defined in claim 1 further comprising selecting the second route based on an identifier associated with the first route.

8. A tangible machine readable storage device storing machine readable instructions which, when executed, cause a machine to perform operations comprising:
   determining whether a sequence number included in a first reroute request received from a second router is newer than a stored sequence number associated with the second router, the first reroute request including network failure information identifying a cause of a failure of a first route, the sequence number being incremented for each new reroute request sent from the second router; and
   selecting a second route from a plurality of routes to carry data in place of the first route if the sequence number included in the first reroute request is determined to be newer than the stored sequence number but not if the sequence number included in the first reroute request is determined to be older than the stored sequence number, the plurality of routes being stored in a routing table, the second route being different from the first route.

9. The storage device as defined in claim 8 wherein the first reroute request comprises information related to a condition of the first route.

10. The storage device as defined in claim 8 wherein the operations further comprise determining a cause of a failure of a third route by detecting a loss of a signal along the third route.

11. The storage device as defined in claim 8 wherein the operations further comprise determining a cause of a failure of a third route by using a link layer failure detection scheme.

12. The storage device as defined in claim 8 wherein the operations further comprise sending a second reroute request to a third system, the second reroute request including information related to a condition of the first route.

13. The storage device as defined in claim 8 wherein the operations further comprise selecting the second route based on the cause of the failure.

14. The storage device as defined in claim 8 wherein the operations further comprise selecting the second route based on an identifier associated with the first route.

15. A first router comprising:
   a memory having machine readable instructions stored thereon; and
   a processor to execute the instructions to perform operations comprising:
      determining whether a sequence number included in a first reroute request received from a second router is newer than a stored sequence number associated with the second router, the first reroute request including network failure information identifying a cause of a failure of a first route, the sequence number being incremented for each new reroute request sent from the second router; and
      selecting a second route from a plurality of routes to carry data in place of the first route if the sequence number included in the first reroute request is determined to be newer than the stored sequence number but not if the sequence number included in the first reroute request is determined to be older than the stored sequence number, the plurality of routes being stored in a routing table, the second route being different from the first route.

16. The first router as defined in claim 15 wherein the first reroute request comprises information related to a condition of the first route.

17. The first router as defined in claim 15 wherein the operations further comprise determining a cause of a failure of a third route by detecting a loss of a signal along the third route.

18. The first router as defined in claim 15 wherein the operations further comprise sending a second reroute request to a third system, the second reroute request including information related to a condition of the first route.

19. The first router as defined in claim 15 wherein the operations further comprise selecting the second route based on the cause of the failure.

20. The first router as defined in claim 15 wherein the operations further comprise selecting the second route based on an identifier associated with the first route.

* * * * *